United States Patent
Michienzi

(10) Patent No.: US 9,188,571 B2
(45) Date of Patent: Nov. 17, 2015

(54) CHROMATOGRAPHY APPARATUS HAVING DIFFUSION BONDED COUPLER

(75) Inventor: Joseph D. Michienzi, Plainville, MA (US)

(73) Assignee: Waters Technologies Corporation, Milford, MA (US)

( * ) Notice: Subject to any disclaimer, the term of this patent is extended or adjusted under 35 U.S.C. 154(b) by 0 days.

(21) Appl. No.: 14/233,033

(22) PCT Filed: Aug. 23, 2012

(86) PCT No.: PCT/US2012/051976
§ 371 (c)(1),
(2), (4) Date: Jan. 15, 2014

(65) Prior Publication Data
US 2014/0157988 A1 Jun. 12, 2014

Related U.S. Application Data

(60) Provisional application No. 61/527,648, filed on Aug. 26, 2011, provisional application No. 61/527,639, filed on Aug. 26, 2011, provisional application No. 61/527,747, filed on Aug. 26, 2011, provisional application No. 61/527,638, filed on Aug. 26, 2011, provisional application No. 61/621,852, filed on Apr. 9, 2012.

(51) Int. Cl.
*G01N 30/60* (2006.01)
*G01N 30/72* (2006.01)
(Continued)

(52) U.S. Cl.
CPC ............... *G01N 30/72* (2013.01); *B01D 15/22* (2013.01); *B05B 5/16* (2013.01); *G01N 30/60* (2013.01);
(Continued)

(58) Field of Classification Search
CPC .............. G01N 30/60; G01N 30/6004; G01N 30/6026; G01N 30/6052; G01N 30/606; G01N 30/6095; B01D 15/22
See application file for complete search history.

(56) References Cited

U.S. PATENT DOCUMENTS 5,750,926 A     5/1998   Schulman et al.
5,766,460 A  *  6/1998   Bergstrom et al. ........ 210/198.2
(Continued)

FOREIGN PATENT DOCUMENTS

WO    2007112224 A2   10/2007
WO    2008106613 A2    9/2008

OTHER PUBLICATIONS

International Preliminary Report on Patentability for counterpart international patent application No. PCT/US12/51976, mailed on Apr. 3, 2014; 6 pages.
(Continued)

*Primary Examiner* — Robert Clemente
(74) *Attorney, Agent, or Firm* — Schmeiser, Olsen & Watts LLP; William G. Guerin

(57) ABSTRACT

Described is a chromatography a chromatography apparatus that includes a microfluidic substrate, a coupler and a sealing fitting. The microfluidic substrate can include one or more chromatography columns, such as analytical columns or trap columns, and an inlet in communication with the one or more chromatography columns. The coupler is diffusion bonded to the surface of the microfluidic substrate so that an opening in the coupler is aligned to the inlet in the microfluidic substrate. The sealing fitting includes a heat-resistant sealant disposed in the opening of the coupler and in contact with the surface of the substrate. The coupler and sealing fitting enable a compact fluid-tight connection to the inlet of the microfluidic substrate that exhibits high tensile and torsional strength, and does not require the use of adhesives.

12 Claims, 3 Drawing Sheets

(51) Int. Cl.
*B01D 15/22* (2006.01)
*B05B 5/16* (2006.01)
*F16L 19/02* (2006.01)
*F16L 9/14* (2006.01)
*B01D 15/18* (2006.01)

(52) U.S. Cl.
CPC ........ *G01N 30/6026* (2013.01); *G01N 30/6052* (2013.01); *B01D 15/1871* (2013.01); *F16L 9/14* (2013.01); *F16L 19/02* (2013.01); *G01N 30/6004* (2013.01); *G01N 30/6039* (2013.01); *G01N 30/6095* (2013.01); *G01N 30/7266* (2013.01); *Y10T 29/49908* (2015.01)

(56) References Cited

U.S. PATENT DOCUMENTS

| | | | |
|---|---|---|---|
| 6,089,617 A * | 7/2000 | Craig et al. | 285/288.1 |
| 6,772,513 B1 | 8/2004 | Frye-Mason et al. | |
| 7,164,572 B1 | 1/2007 | Burdon et al. | |
| 7,607,223 B2 | 10/2009 | Pleskach et al. | |
| 2003/0072679 A1 | 4/2003 | Johnson et al. | |
| 2007/0277374 A1 | 12/2007 | Suaning | |
| 2009/0314065 A1* | 12/2009 | Kiyomoto et al. | 73/61.53 |
| 2010/0171055 A1 | 7/2010 | Dourdeville | |

OTHER PUBLICATIONS

International Search Report and Written Opinion in related international patent application No. PCT/US12/151976, mailed on Nov. 2, 2014; 7 pages.

Extended Search Report in counterpart European Patent Application No. 12826759.8, mailed on May 29, 2015; 6 pages.

Haapala, et al., "Microchip for Combining Gas Chromatography or Capillary Liquid Chromatography with Atmospheric Pressure Photoionization-Mass Spectrometry", Analytical Chemistry, Jul. 1, 2007, vol. 79, No. 13, pp. 4994-4999.

* cited by examiner

CHROMATOGRAPHY APPARATUS HAVING DIFFUSION BONDED COUPLER

RELATED APPLICATIONS

This application claims the benefit of the earlier filing date of U.S. Provisional Patent Application Ser. No. 61/527,638, filed Aug. 26, 2011 and titled "Reusable Fitting for Attaching a Conduit to a Port," U.S. Provisional Patent Application Ser. No. 61/527,639, filed Aug. 26, 2011 and titled "Chromatography Apparatus with Diffusion-Bonded Coupler," U.S. Provisional Patent Application Ser. No. 61/527,747, filed Aug. 26, 2011 and titled "Liquid-Chromatography Conduit Assemblies Having High-Pressure Seals," U.S. Provisional Patent Application Ser. No. 61/527,648, filed Aug. 26, 2011 and titled "Electrospray Assembly for a Microfluidic Chromatography Apparatus," and U.S. Provisional Patent Application Ser. No. 61/621,852, filed Apr. 9, 2012 and titled "Chromatography Column Assembly," the entireties of which are incorporated herein by reference.

FIELD OF THE INVENTION

The invention relates generally to a chromatography apparatus. More particularly, the invention relates to a compact chromatography device that can operate at high temperatures.

BACKGROUND

Capillary chromatography, based on either liquid chromatography (LC) or gas chromatography (GC), is advantageous over conventional analytical-scale chromatography in many aspects. For example, capillary chromatography utilizes a low sample volume, low consumption of solvent and is capable of trace analysis. Capillary chromatography, when coupled with mass spectrometry, for example, capillary LC coupled with electrospray ionization-mass spectrometry (ESI-MS) and capillary GC with electron ionization mass spectrometry (EI-MS), results in good MS detection sensitivity because the low flow rate of capillary LC or GC is compatible with the ion source input rates of ESI-MS and EI-MS.

LC and GC differ in a number of ways, such as mobile-phase viscosity, average diffusion coefficient of a sample in the mobile phase and mobile-phase compressibility. One significant difference is that GC generally is used with samples which are volatile, can be evaporated intact at high temperatures or from which volatile derivatives can be reliably obtained. Consequently, GC devices typically operate at substantially higher temperatures than LC devices.

Despite many advantages of capillary LC and GC, chromatographers tend to make use of analytical-scale chromatography systems whenever possible because both capillary LC and GC also present difficult challenges. As an example, fused-silica tubes are commonly used in a capillary chromatography system due to their desirable features. The dimensions of fused silica tubing can be easily controlled during manufacturing. Moreover, the wall of a fused-silica tube is clean, non-reactive and smooth, providing good transport of small volumes of fluids. Unfortunately, fused-silica tubes are small, fragile and brittle. Thus an operator must be experienced and exercise due care to properly make fluidic connections using fused-silica tubes.

Capillary LC or GC systems operate at low flow rates, typically micro-scale or nano-scale flows, thus what would otherwise be considered leaks or void volumes can still degrade system performance parameters significantly, including chromatographic resolution and detection sensitivity. Moreover, the higher operational temperatures (e.g., greater than 300° C.) of capillary GC systems can induce deformation of fluidic system components and thus such systems are more susceptible to fluidic leaks.

SUMMARY

In one aspect, the invention features a chromatography apparatus that includes a microfluidic substrate, a coupler and a sealing fitting. The microfluidic substrate includes a ceramic material having a chromatography column. The ceramic material has a surface with an inlet that is in fluidic communication with the chromatography column. The coupler includes a metal body with an opening therethrough. The metal body has a surface that is diffusion bonded to the surface of the microfluidic substrate so that the opening in the coupler is aligned to the inlet of the microfluidic substrate. The sealing fitting includes a heat-resistant sealant that is disposed in the opening of the coupler and is in contact with the surface of the substrate.

In another aspect, the invention features a chromatographic apparatus that includes a microfluidic substrate, a coupler, a sealing fitting, a connector and a fitting. The microfluidic substrate includes a ceramic material having a chromatography column. The ceramic material has a surface with an inlet that is in fluidic communication with the chromatography column. The coupler includes a metal body having a hollow cylindrical shape. The metal body has a surface that is diffusion bonded to the surface of the microfluidic substrate in a location so that the metal body is aligned to the inlet of the microfluidic substrate. The sealing fitting includes a heat-resistant polymer and is disposed in the metal body of the coupler in contact with the surface of the substrate. The sealing fitting has a passageway to pass a conduit. The connector has an opening therethrough and is secured to the coupler. The connector is configured to urge the sealing fitting toward the surface of the ceramic material of the microfluidic structure. The fitting is secured to the connector and has a ferrule portion at one end through which the conduit extends to pass through the passageway of the sealing fitting and to be in fluidic communication with the inlet of the microfluidic substrate.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Figure 1:
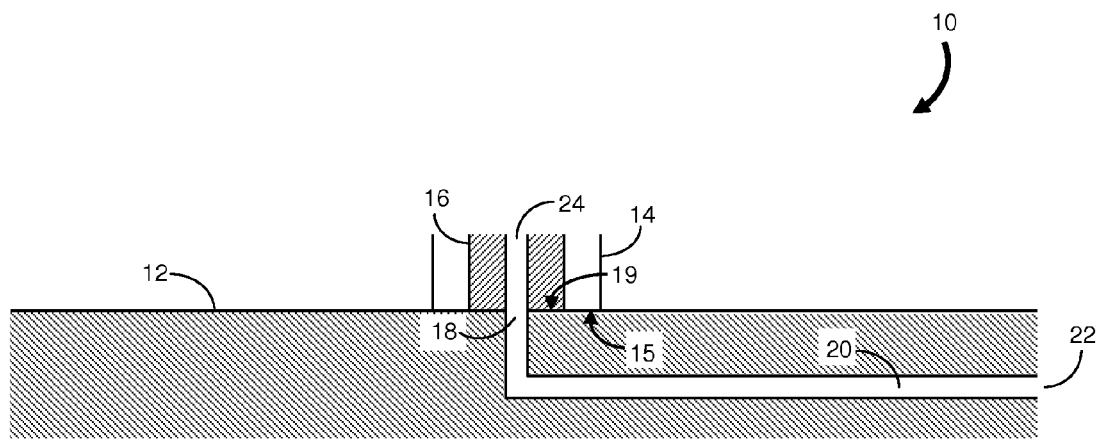
FIG. 1 is a cross-sectional view of a portion of a chromatography apparatus according to one embodiment of the invention.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

The term "capillary", as used herein, refers to tubes or columns having an inner diameter of no greater than about 300 μm. Depending on context, the words "capillary" and "conduit" are used interchangeably herein.

The term "microfluidic substrate", as used herein, refers to any device or processing-unit that performs basic chromatographic work primarily separating a sample into its constituent parts.

The terms "coupler" and "connector", as used herein, refer to any object or mechanism, or part of an object or mechanism, which joins pieces together or connects one mechanical part to another.

The term "opening", as used herein, means a passageway, bore, hole, void and the like in a object that may be occupied by or passed through by another object, a fluid or a gas.

The term "substantially", as used herein, may be applied to modify any quantitative representation which can permissibly vary without resulting in a change in the basic function to which it is related. All numbers may be read as if prefaced by the word "about" even if the word does not expressly appear. Also, any numerical range recited herein is intended to include all sub-ranges subsumed therein.

In brief overview, the invention relates to a chromatography apparatus that includes a microfluidic substrate, a coupler and a sealing fitting. The microfluidic substrate can include one or more chromatography columns (e.g., analytical columns and trap columns) in communication with each other and an inlet in communication with the one or more chromatography columns. The coupler is diffusion bonded to the surface of the microfluidic substrate so that an opening in the coupler is aligned to the inlet in the microfluidic substrate. The sealing fitting includes a heat-resistant sealant disposed in the opening of the coupler and in contact with the surface of the substrate. The coupler and sealing fitting enable a compact fluid-tight connection to the inlet of the microfluidic substrate that exhibits high tensile and torsional strength, and does not require the use of adhesives.

Thus a compact chromatographic apparatus constructed in accordance with the principles of the invention can reduce or eliminate possible leaking spots and void volumes, and ensures that no bare tubing is exposed so as to prevent the apparatus from being damaged in use. In addition, the opportunity for human error leading to improper connections and degraded chromatographic performance is reduced. The apparatus is capable of operation at high temperatures in excess of 300° C.

FIG. 1 provides a cross-sectional view of a chromatography apparatus 10 according to an embodiment of the invention. The apparatus 10 includes a microfluidic substrate 12, a coupler 14 and a sealing fitting 16. A "microfluidic substrate," as used herein, is any substrate that includes one or more fluidic paths having a small equivalent diameter, for example, an equivalent diameter of 300 μm or less. By way of a particular example, the microfluidic substrate 12 can be a chromatographic substrate that includes one or more chromatography columns (not shown) that are in fluidic communication with each other and which are configured to separate a sample into individual sample components. The chromatography columns can be, for example, traps or analytical columns.

The microfluidic substrate 12 in the illustrated embodiment is formed from a ceramic material and includes an inlet 18. In some embodiments, the inlet 18 is in fluidic communication with one or more chromatography columns and the substrate 12 may include heating and temperature control elements (not shown) adapted for use in a high temperature GC system. In some further embodiments, heating elements integrated into the substrate 12 are configured to heat the substrate to a temperature greater than 300° C. The one or more columns are connected to each other through fluidic connection components (not shown), such as conduits, valves, tees and the like. The combination of fluidic components defines a fluidic path 20 from the inlet 18 to an outlet 22. A fluid that flows through the fluidic path 20 and exits at the outlet 22 can be directed through a conduit or other fluidic channel toward a detector such as a MS instrument. A "MS instrument," as used herein, refers to any detection apparatus or device for ionizing chemical compounds in a sample to generate charged molecules or molecule fragments, and determining the mass-to-charge ratios of the charged molecules or molecule fragments. When the chromatography apparatus is coupled with a MS instrument, for example, an ESI-MS instrument, the ion probe tip can be either integral to or separate from the microfluidic substrate 12.

The coupler 14 is formed of a metal, preferably titanium, and has an opening between its upper surface (not shown) and lower surface 15. The diffusion temperature of the metal coupler 14 is less than the sintering temperature of the ceramic substrate 12. The lower surface 15 of the metal coupler 14 is diffusion bonded to the microfluidic substrate 12 at the interface of the metal and ceramic materials so that the coupler opening is coaxially aligned with the inlet 18. In addition, the surface 19 of the substrate 12 is rougher than the surface 15 of the coupler 14 at the bond interface. The surface roughness, expressed as the average of the peak to valley variations, of the substrate 12 is preferably greater than 0.75 μm.

The diffusion bond is preferred over other bonding techniques such as brazing or use of adhesives. Brazing requires additional materials to create a joint. Adhesives are generally limited to temperatures below 300° C. and lose strength with increasing temperature. In contrast, the diffusion bond has high tensile and torsional strength, and is stable at temperatures greater than 300° C.

In one example of a process for creating a diffusion bond between the ceramic substrate 12 and the metal coupler 14, the surfaces to be bonded are cleaned using a solvent (e.g., a solvent of 2-propanol). The cleaned surfaces of the ceramic substrate 12 and metal coupler 14 are then pressed against each other using an applied constant force in a range from about 500 psi to about 1,000 psi while heating the substrate 12 and coupler 14 to a diffusion temperature that is less than the melting point of the metal. The applied temperature and pressure are maintained for approximately ten hours before returning to ambient temperature (e.g., 25° C.).

The sealing fitting 16 is formed of a heat-resistant polymer or other suitable heat-resistant sealant material and is disposed in the opening of the coupler 14 to be in direct contact with the surface 19 of the microfluidic substrate 12. A preferred heat-resistant material is graphite loaded poly-oxy-diphenylene-pyromellitimide (available, for example, as VESPEL® SP-21 from DuPont Engineering Polymers of Newark, Del. which is stable at temperatures greater than 300° C. In the illustrated embodiment, the sealing fitting 16 is a cylindrically-shaped element and has a passageway 24 (i.e., bore) between its upper and lower surfaces that is coaxially aligned with the opening through the coupler 14 and the inlet 18 of the substrate 12.

A conduit coupled to a fluid source can be inserted into the passageway 24 of the sealing fitting 16 to convey a fluid to the inlet 18 of the substrate 12. Although the diameter of the passageway 24 is shown to be approximately equal to the diameter of the fluidic path 20, in general these diameters can be different. The conduit can be directed into the sealing fitting 16 by a fitting or the like, along with other fluidic components, such as connectors, unions and tees. For example, when a fitting with a ferrule is used to direct the conduit, a portion of the conduit that extends beyond the ferrule is received in the passageway 24 of the sealing fitting 16. While securing the fitting relative to the substrate 12, either directly or through an intermediate fluidic component such as a connector, the conduit is urged toward the substrate 12 until the end of the conduit abuts the substrate 12 at the inlet 18. Meanwhile, the sealing fitting 16 is pressed by the fitting downward inside the coupler 14 and against the surface 19 of the substrate 12 to seal the conduit to the inlet 18.

Figure 2:
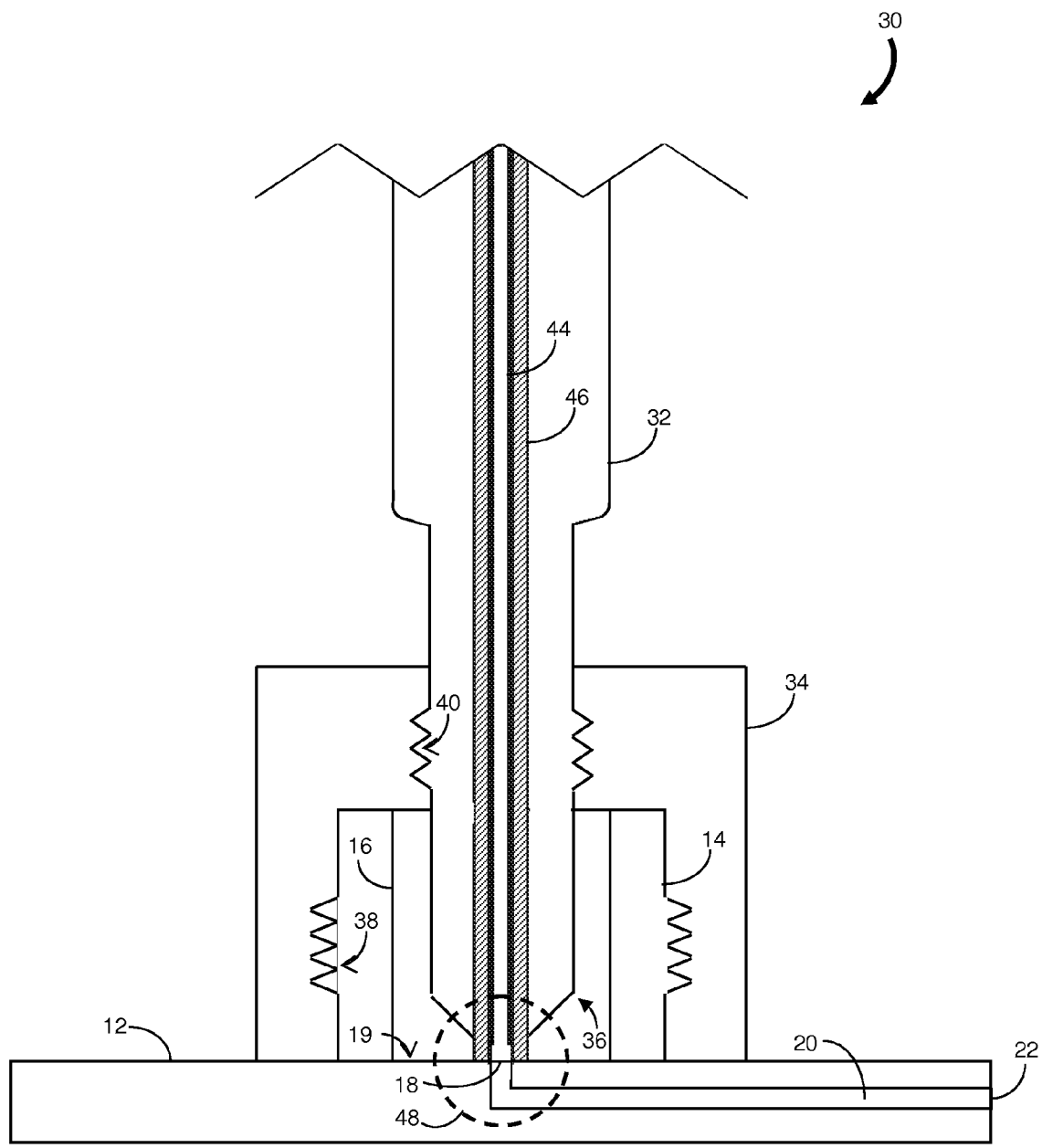
FIG. 2 is a cross-sectional view of a chromatography apparatus according to another embodiment of the invention.

FIG. 2 is a cross-sectional view of a chromatography apparatus 30 according to another embodiment of the invention. In addition to elements similar to those shown in FIG. 1, the chromatography apparatus 30 includes a fitting 32 and a connector 34.

As illustrated, the fitting 32 is a one-piece fitting having a ferrule portion 36 which is integral to an end of the fitting 32. In alternative embodiments, a fitting can have two or more pieces. For example, a ferrule can be a separate piece from the fitting body. The fitting 32 can be fabricated of any suitable material, including a polymer, a metal or a combination of polymer and/or metal materials.

The connector 34 has a threaded inner surface 38 to engage a threaded portion of the outer surface of the coupler 14 to thereby secure the two components to each other. The connector 34 also has a threaded surface 40 that surrounds an opening that allows a portion of the fitting 32 to extend into the sealing fitting 16. Threads along a portion of an outer surface of the fitting 32 engage the threaded surface 40 at the opening to thereby secure the fitting 32 to the connector 34.

A conduit 44 disposed in a metal sleeve 46 is held in the fitting 32. During installation, the connector 34 and fitting 32 press the sealing fitting 16 against the surface 19 of the microfluidic substrate 12 to seal the connection between the end of the conduit 44 and the inlet 18 of the substrate 12 so that substantially no void volume is present at the connection.

Figure 3:
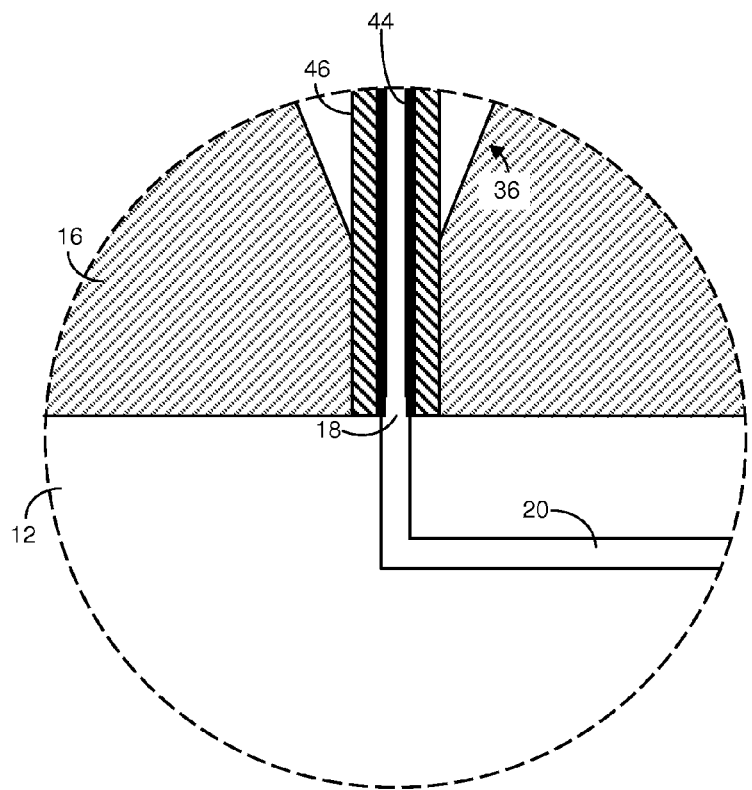
FIG. 3 is a magnified view of a region of the chromatography apparatus shown of FIG. 2.

FIG. 3 shows a magnified view of the region within the dashed circle 48 of FIG. 2. The portion of the conduit 44 that extends from the fitting 32 is received in the passageway of the sealing fitting 16. The passageway of the sealing fitting 16 is aligned with the inlet 18 of the substrate 12 such that the end of the conduit 44 abuts or extends a short distance into the inlet 18 to form a fluid-tight seal and a continuous fluidic path of minimal void volume.

Figure 4:
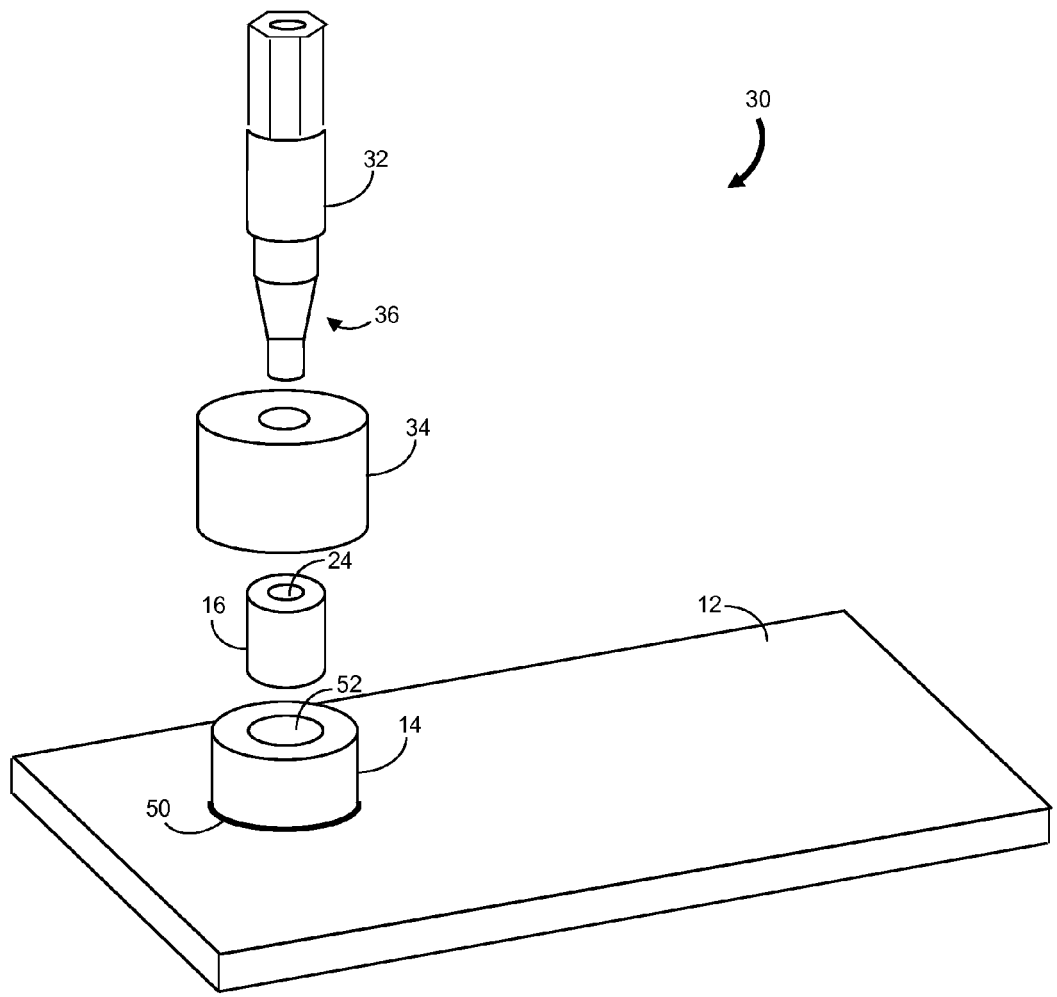
FIG. 4 is an exploded three-dimensional view of the chromatography apparatus of FIG. 2.

Reference is made to FIG. 4, which is an exploded three-dimensional view of the chromatography apparatus 30 of FIG. 2, to show assembly of the chromatography apparatus 30 by a series of steps. First, the metal coupler 14 is diffusion bonded to a surface 19 of the ceramic substrate 12 so that the opening in the coupler 14 is coaxially aligned with the inlet (not visible) of the microfluidic substrate 12. The diffusion bond is formed (at bond line 50), for example, as described above for FIG. 1 using certain pressure and temperature. Upon completion of the diffusion bonding process, the sealing fitting 16 is placed inside the opening 52 through the coupler 14 before threading the connector 34 onto the coupler 14. Subsequently, the fitting 32 is threaded into the connector 34 so that the ferrule portion 36 is first received in the passageway 24 of the sealing fitting 16. Continued threading of the fitting 32 into the connector 34 results in the sealing fitting 16 being pressed against the surface of the ceramic substrate 12 to achieve a fluid-tight seal at the inlet that can withstand high operating temperatures.

In various embodiments, the chromatographic apparatus 30 is part of a high performance liquid chromatography (HPLC) system, or an ACQUITY UPLC® or nanoACQUITY UPLC® system (available from Waters Corporation of Milford, Mass.). In other embodiments, the chromatographic apparatus 30 is a capillary GC system that can operate at high temperatures that may exceed 300° C.

In some embodiments, the apparatus 30 is configured to interface with a MS instrument. For example, the chromatography apparatus 30, used in a capillary LC system, can be coupled to an ESI-MS instrument. In a typical ESI-MS process, a liquid sample is pumped through an emitter (e.g., a stainless-steel needle) having a high applied voltage such that the liquid sample is transformed into a mist of charged droplets. As the charged droplets evaporate, the repulsion of electric charges on each droplet grows stronger than the surface tension holding the droplet together. The droplets separate into a thin aerosol cloud comprising very small charged particles which are directed into a mass spectrometer. In some embodiments, the emitter is integrated into the microfluidic substrate of the apparatus.

When implemented in a capillary GC system, the chromatography apparatus 30 can be coupled with an EI-MS instrument. In a typical EI-MS process, ionization occurs when a sample is exposed to energetic electrons emitted from an electron emitter. The interaction of the electrons with the sample breaks the molecular bonds of the sample molecules to produce ions. In some embodiments, the electron emitter is integrated into the microfluidic substrate of the apparatus.

The chromatography apparatus 30 can be configured to interface with a light detection instrument. The term "light detection instrument", as used herein, refers to any device responsive to light energy or optical radiation, or capable of determining the intensity of light incident on the device. A light detection instrument can be, by way of non-limiting examples, an ultraviolet (UV) detector, an infrared (IR) detector, or a UV-visible detector.

Other detection devices and instruments are contemplated for use with the chromatography apparatus 30, such as devices and instruments utilizing Raman spectroscopy and nuclear magnetic resonance (NMR) techniques.

While the invention has been shown and described with reference to specific embodiments, it should be understood by those skilled in the art that various changes in form and detail may be made therein without departing from the spirit and scope of the invention as recited in the accompanying claims. For example, though embodiments described above include a sealing fitting having a cylindrical shape, the invention contemplates sealing fittings having other shapes that can also achieve a fluid-tight seal at the inlet of the substrate. In another example, though the connector is described in embodiments above as being secured to the coupler via mating threads, a connector can be tightened onto a coupler by other means, such as welding or clamping.

What is claimed is:

1. A chromatography apparatus, comprising:
a microfluidic substrate comprising a ceramic material having a chromatography column therein, the ceramic material having a flat surface with an inlet therein that is in fluidic communication with the chromatography column;
a coupler comprising a metal body with an opening therethrough, the metal body having a flat surface that is diffusion bonded to the flat surface of the microfluidic substrate so that the opening in the coupler is aligned to the inlet of the microfluidic substrate; and
a sealing fitting comprising a heat-resistant sealant disposed in the opening of the coupler and being in contact with the flat surface of the substrate.

2. The chromatography apparatus of claim 1 wherein the metal body comprises titanium.

3. The chromatography apparatus of claim 1 wherein the heat-resistant sealant is a heat-resistant polymer.

4. The chromatography apparatus of claim 1 wherein the microfluidic substrate has a heating element to heat the microfluidic substrate to at least 300° C.

5. The chromatography apparatus of claim 1 wherein the heat-resistant polymer is graphite loaded poly-oxydiphenylene-pyromellitimide.

6. The chromatography apparatus of claim 1 wherein the sealing fitting comprises graphite.

7. The chromatography apparatus of claim 1 further comprising a fitting in communication with the sealing fitting and configured to dispose a conduit in fluidic communication with the inlet of the microfluidic substrate.

8. The chromatography apparatus of claim 7 wherein the fitting is configured to receive a sleeve around a portion of the conduit.

9. The chromatography apparatus of claim 7 wherein the fitting has a ferrule portion at one end through which the conduit extends to be in fluidic communication with the inlet of the microfluidic substrate.

10. The chromatography apparatus of claim 9 further comprising a connector having an opening therethrough to pass the ferrule portion of the fitting and to press the ferrule portion of the fitting against the sealing fitting.

11. The chromatography apparatus of claim 10 wherein the sealing fitting has a passageway therein to receive the ferrule portion of the fitting and wherein the conduit that extends from the ferrule portion has an end that substantially abuts the inlet of the microfluidic substrate to form a fluidic connection, wherein the sealing fitting is pressed by the fitting against the flat surface of the substrate to achieve a fluid-tight seal at the inlet of the substrate.

12. A chromatographic apparatus, comprising:
a microfluidic substrate comprising a ceramic material having a chromatography column therein, the ceramic material having a surface with an inlet therein that is in fluidic communication with the chromatography column;
a coupler comprising a metal body having a hollow cylindrical shape, the metal body having a flat surface that is diffusion bonded to the surface of the microfluidic substrate in a location so that the metal body is aligned to the inlet of the microfluidic substrate;
a sealing fitting comprising a heat-resistant polymer and disposed in the metal body of the coupler in contact with the flat surface of the substrate, the sealing fitting having a passageway to pass a conduit;
a connector having an opening therethrough and being secured to the coupler, the connector configured to urge the sealing fitting toward the flat surface of the ceramic material of the microfluidic structure; and
a fitting secured to the connector and having a ferrule portion at one end through which the conduit extends to pass through the passageway of the sealing fitting and to be in fluidic communication with the inlet of the microfluidic substrate.

* * * * *